US009316615B2

(12) United States Patent
Tajima

(10) Patent No.: US 9,316,615 B2
(45) Date of Patent: Apr. 19, 2016

(54) DEVICE FOR TRAPPING BIOLOGICALLY-RELEVANT SUBSTANCES AND SYSTEM FOR COLLECTING BIOLOGICALLY-RELEVANT SUBSTANCES

(75) Inventor: Hideji Tajima, Matsudo (JP)

(73) Assignee: Universal Bio Research Co., Ltd., Chiba (JP)

( * ) Notice: Subject to any disclaimer, the term of this patent is extended or adjusted under 35 U.S.C. 154(b) by 553 days.

(21) Appl. No.: 13/805,382

(22) PCT Filed: Jun. 22, 2011

(86) PCT No.: PCT/JP2011/064255
§ 371 (c)(1),
(2), (4) Date: Feb. 1, 2013

(87) PCT Pub. No.: WO2011/162290
PCT Pub. Date: Dec. 29, 2011

(65) Prior Publication Data
US 2013/0140183 A1   Jun. 6, 2013

(30) Foreign Application Priority Data
Jun. 22, 2010 (JP) .................. 2010-141779

(51) Int. Cl.
G01N 27/447 (2006.01)
G01N 33/553 (2006.01)
(Continued)

(52) U.S. Cl.
CPC ........ G01N 27/447 (2013.01); G01N 27/44739 (2013.01); G01N 1/02 (2013.01); G01N 33/553 (2013.01); G01N 35/0098 (2013.01)

(58) Field of Classification Search
CPC . G01N 27/447; G01N 27/44739; G01N 1/02; G01N 35/0098; G01N 27/44786; G01N 15/0656
USPC ......................................... 436/526
See application file for complete search history.

(56) References Cited

U.S. PATENT DOCUMENTS 5,702,950 A      12/1997  Tajima
6,468,810 B1 *   10/2002  Korpela ................. B03C 1/284
                                                          210/224
2004/0203126 A1  10/2004  Fukushima

FOREIGN PATENT DOCUMENTS

JP    1993-088296       12/1993
JP    2005-88296    *   12/1993  ............... C12M 1/00
(Continued)

OTHER PUBLICATIONS

Yu et al. (Sensors and Actuators B, 113, 2006, 749-754).*
(Continued)

Primary Examiner — Luan Van
Assistant Examiner — Steven Rosenwald
(74) Attorney, Agent, or Firm — Fish & Richardson P.C.

(57) ABSTRACT

The disclosed device for trapping biologically-relevant substances can easily collect biologically-relevant substances from a thin tissue section or a gel in which said biologically-relevant substance have been fractionated. Said device is provided with: trapping bodies for trapping biologically-relevant substances; carriers that hold the trapping bodies; and electrodes for charging the trapping bodies. The trapping bodies are charged and brought into contact with a prescribed position on a thin tissue section that contains biologically-relevant substances or a gel in which biologically-relevant substances have been fractionated, thereby trapping said biologically-relevant substances from said gel or thin tissue section.

7 Claims, 14 Drawing Sheets

(51) Int. Cl.
*G01N 1/02* (2006.01)
*G01N 35/00* (2006.01)

(56) References Cited

FOREIGN PATENT DOCUMENTS

| JP | 8-62224 | | 3/1996 | |
|---|---|---|---|---|
| JP | 09-15206 | | 1/1997 | |
| JP | 09-015206 | * | 1/1997 | ........... G01N 27/447 |
| JP | 2000-206009 | | 7/2000 | |
| JP | 2004-309325 | | 11/2004 | |
| JP | 2005-069905 | | 3/2005 | |
| JP | 2006-112847 | | 4/2006 | |
| JP | 2009-541734 | | 11/2009 | |
| WO | WO2008/010111 | | 1/2008 | |

OTHER PUBLICATIONS

Miyabayashi et al. (Anal. Chim Acta, 213, 1988, 121-130).*
Saiyed et al. (Anal. Biochem. 363, 2007, 288-290).*
International Search Report dated Jul. 19, 2011 issued in corresponding PCT Application No. PCT/JP2011/064255.

* cited by examiner

M1: Molecular weight marker 1 (λDNA/Hind III Marker)
HG: Control Human Genome DNA (Roche)
PCR: PCR Product (1038bp)
M2: Molecular weight marker 2 (Wide-Range DNA Ladder)

DEVICE FOR TRAPPING BIOLOGICALLY-RELEVANT SUBSTANCES AND SYSTEM FOR COLLECTING BIOLOGICALLY-RELEVANT SUBSTANCES

CROSS-REFERENCE TO RELATED APPLICATIONS

This is the U.S. National Phase, submitted pursuant to 35 U.S.C. §371, of International Patent Application No. PCT/JP2011/064255 filed on Jun. 22, 2011, which claims priority to application no. JP 2010-141779 filed in Japan on Jun. 22, 2010.

TECHNICAL FIELD

The present invention relates to a device for collecting a biologically-relevant substance from a gel in which said biologically-relevant substance has been distributed.

BACKGROUND ART

Electrophoresis is a well known method for fractionating a biologically-relevant substance such as a protein or a nucleic acid. According to such an electrophoresis, proteins or nucleic acids are fractionated on a planar gel such as a polyacrylamide gel or an agarose gel based on molecular weight, molecular shape, electric charge or the like. Recently, further research has been carried out on techniques for fractionating a biologically-relevant substance on a gel with a fractionation device, acquiring the fractionated biologically-relevant substance from the gel, and supplying it to an analyzer such as a mass spectrometer (mass spectrometry) for analysis.

In order to supply the fractionated biologically-relevant substance to the analyzer, the fractionated biologically-relevant substance needs to be collected from the planar gel. For example, according to Southern blotting or Western blotting, a membrane filter is placed on the fractionated planar gel to integrate the gel with the membrane filter, to which positive and negative charges are applied on both surfaces to transfer the biologically-relevant substance from the gel to the membrane filter. Subsequently, positions of the spots are confirmed and the biologically-relevant substance of interest is labeled with a probe or an antibody to perform extraction and the extract is subjected to mass spectrometry.

Thus, conventionally, a large number of steps are required from fractionation to analysis with most of the steps being manually carried out, requiring time and labor.

Also as a technique for collecting a biologically-relevant substance fraction that fractionated on a gel, an excision tool such as a scalpel is used to excise the biologically-relevant substance from the gel, and the excised biologically-relevant substance is subjected to an analyzer for analysis. Another device is also considered which blows gas from a nozzle to excise the fraction on the gel (Patent Document 1).

Such excision operations, however, are also cumbersome. Moreover, if the biologically-relevant substance fraction is to be manually excised, it is even more troublesome and causes collection of unnecessary components that may reduce the precision of the analysis.

PRIOR ART DOCUMENT

Patent Document

[Patent Document]
[Patent Document 1] Japanese Patent Application Publication No. 2005-069905

SUMMARY OF THE INVENTION

Problem to be Solved by the Invention

Hence, the present invention has an objective of providing a device for trapping a biologically-relevant substance and a system for collecting a biologically-relevant substance, which allow easy acquisition of the biologically-relevant substance of interest from a gel or a thin tissue section having a fractionation pattern formed thereon.

Means for Solving Problems

In order to accomplish the above-described objective, the present invention provides a device for trapping a biologically-relevant substance, comprising: trapping bodies for trapping the biologically-relevant substance; a carrier retaining the trapping bodies; and an electrode for charging the trapping bodies,
wherein the trapping bodies are charged and brought into contact with a predetermined position on a gel in which the biologically-relevant substance has been fractionated or a thin tissue section containing the biologically-relevant substance so as to trap the biologically-relevant substance from said gel or thin tissue section.

In the trapping device of the present invention, the trapping bodies may be magnetic particles or magnetic particles bound with a substance having affinity for the biologically-relevant substance.

According to the present invention, the carrier is, for example, a magnet or a combination of a magnet and a conductive member. The trapping bodies are charged, for example, via the carrier. This carrier may further be provided with a mechanism for magnetizing or demagnetizing the trapping bodies. Examples of the biologically-relevant substances include nucleic acids or proteins.

In addition, the present invention is a system for collecting a biologically-relevant substance, comprising:
a trapping device, including (a) magnetic particles for trapping a biologically relevant substance; (b) a rod-like magnetic member being capable of retaining the magnetic particles on a tip of the magnetic member and releasing the magnetic particles from the tip; and (c) an electrode for charging the magnetic member. In use, the magnetic particles retained by the magnetic member are charged and brought into contact with (i) a predetermined position on a gel in which the biologically-relevant substance has been fractionated or (ii) a thin tissue section containing the biologically-relevant substance such that the biologically-relevant substance from the gel or thin tissue section is trapped.

a position designating means for assigning the trapping bodies of the trapping device to a predetermined position on a thin tissue section or a gel in which a biologically-relevant substance has been distributed or to each of segments that have been sectionalized into predetermined sections;

a contact control means for bringing the trapping bodies into contact with the assigned position or segment; and a collecting means for trapping and collecting the biologically-relevant substance from said trapping bodies that made contact with said position or segment.

Here, the collection system of the present invention may have an image sensor for taking an image of a gel in which the biologically-relevant substance has been fractionated or a thin tissue section containing the biologically-relevant substance.

Furthermore, the system of the present invention may also have a designating means for designating a position for acquiring the biologically-relevant substance on the taken image.

In addition, in the collection system of the present invention, the position designating means comprises:

an image sensor for taking an image of a thin tissue section or a gel in which the biologically-relevant substance has been distributed; and a coordinates calculating means for determining the position for acquiring the biologically-relevant substance on the image of the gel or the thin tissue section generated based on the image signal from the image sensor and figuring out the coordinates corresponding to the acquisition position on the gel or the thin tissue section, wherein the contact control means may move the trapping bodies to the coordinates figured out by the coordinates calculating means.

With these collection systems of the present invention, a biologically-relevant substance can be obtained automatically.

Furthermore, the present invention also provides a method for collecting a biologically-relevant substance, comprising a step of collecting the biologically-relevant substance from a gel in which the biologically-relevant substance has been fractionated or a thin tissue section containing the biologically-relevant substance by using the above-described trapping device or collection system.

Effect of the Invention

The trapping device of the present invention can utilize electric action or chemical interaction, for example, affinity, between the trapping bodies and a biologically-relevant substance so that the biologically-relevant substance of interest can simply and selectively be collected from a thin tissue section or a gel in which the biologically-relevant substance has been distributed.

The trapping device of the present invention assigns the trapping bodies to respective segments of a gel or a thin tissue section that has been sectionalized into a matrix so as to bring each of the trapping bodies into contact with the segment to trap the biologically-relevant substance. Thus, a biologically-relevant substance can be collected from a gel or a thin tissue section having any fractionation pattern.

In addition, the trapping device of the present invention figures out the coordinates on the actual gel or thin tissue section based on the position for acquiring the biologically-relevant substance determined on an image of the gel or the thin tissue section, and brings the trapping bodies into contact with the coordinates to trap the biologically-relevant substance. Thus, a biologically-relevant substance can be collected from any position on the gel or the thin tissue section.

In this way, the device of the present invention can be used to automate collection of a biologically-relevant substance from a gel or a thin tissue section, thereby simplifying the operations.

EMBODIMENTS FOR CARRYING OUT THE INVENTION

1. General Outline

Figure 1:
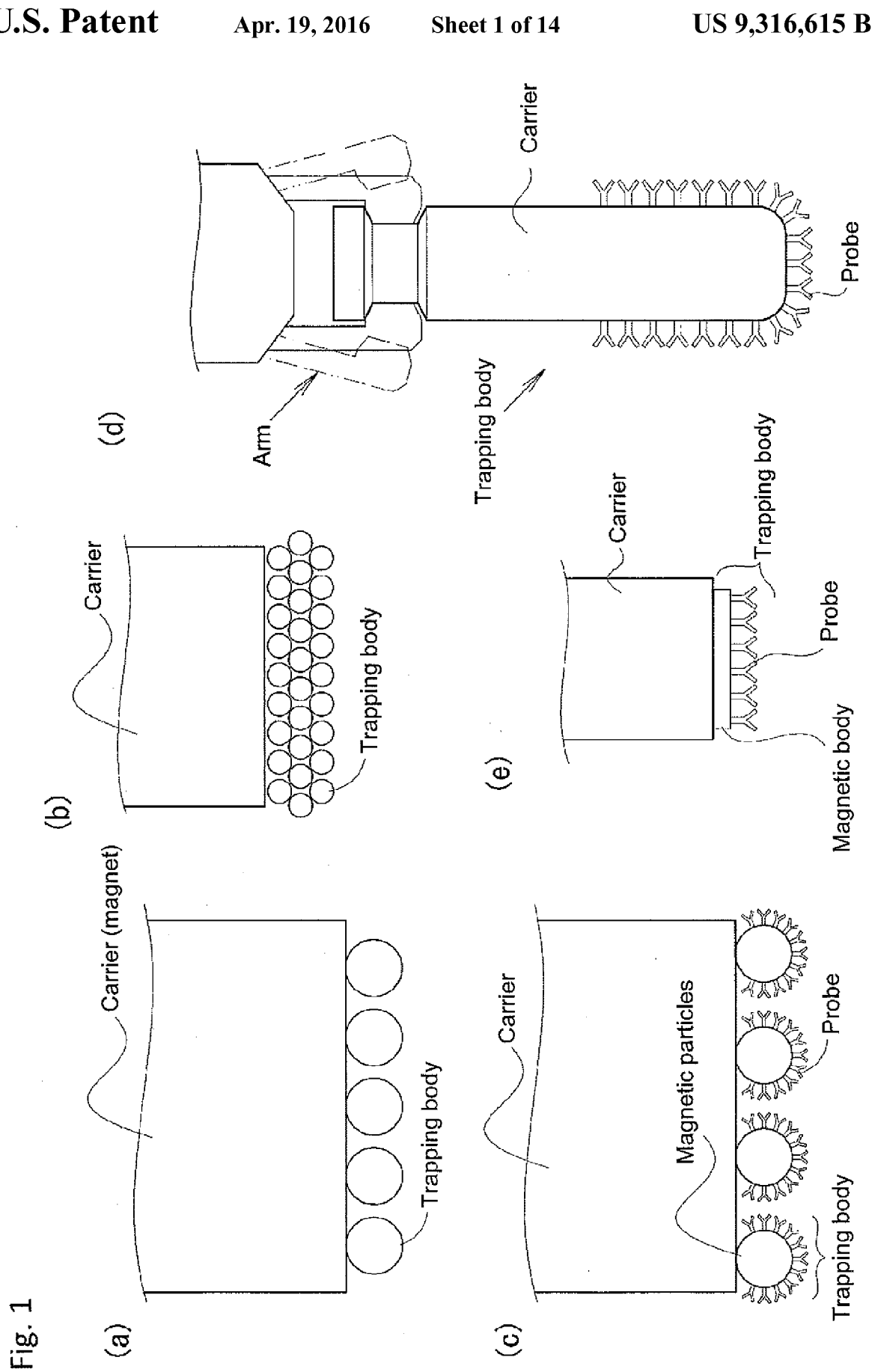
FIG. 1 Illustrative drawings showing embodiments of trapping bodies according to the present invention.

The present invention is a device for trapping a biologically-relevant substance, comprising: trapping bodies for trapping the biologically-relevant substance; a carrier for retaining the trapping bodies; and an electrode for charging the trapping bodies.

The trapping bodies are charged and brought into contact with a predetermined position on a gel in which the biologically-relevant substance has been fractionated or a thin tissue section containing the biologically-relevant substance, thereby trapping the biologically-relevant substance from said gel or thin tissue section.

In a device of the present invention, the trapping bodies are magnetic or conductive particles, preferably magnetic particles. The trapping bodies are retained in the carrier and charged by the electrode upon trapping the biologically-relevant substance.

The present invention provides a device or a method for acquiring a biologically-relevant substance from a given area, intending whole or a part of a thin tissue section or a gel in which the biologically-relevant substance has been distributed. According to the present invention, a biologically-relevant substance is collected based on the principle where the biologically-relevant substance is adsorbed onto trapping bodies through electric interaction between positively or negatively charged biologically-relevant substance and oppositely charged trapping bodies or the principle where the biologically-relevant substance is trapped by a substance having affinity for the biologically-relevant substance bound to the trapping bodies.

As described above, conventional steps of collecting and analyzing a biologically-relevant substance sample that has been fractionated by Southern blotting or Western blotting are carried out manually. According to the present invention, these operations can be carried out mechanically (i.e., processed automatically). Trapping bodies of the present invention are alternative to a membrane filter that has been used in conventional blotting. Use of the trapping bodies of the present invention saves the trouble of using a filter, and thus the operation can considerably be simplified.

Here, we focus on an embodiment of collecting a biologically-relevant substance (e.g., DNA) that has been fractionated on a gel by using a (rod-like) magnetic member as a carrier and magnetic particles retained on the tip of the magnetic member as trapping bodies.

The magnetic member may be a permanent magnet, an electromagnet or the like, and may comprise any material that generates magnetic force for adsorbing and retaining the magnetic particles. Since the trapping bodies are magnetic particles, these particles are attracted to and retained on the tip of the magnetic member. In one embodiment of the present invention, the carrier is connected to an electrode. A current from the electrode flows to the magnetic particles via the carrier to charge the magnetic particles. Simultaneously with or before or after this charging, the magnetic particles are brought into contact with a gel so that the negatively charged DNA moves to the positive electrode side (trapping body side) while using water in the gel as a medium so as to be adsorbed onto the positively charged magnetic particles via electric interaction.

Subsequent to adsorption, the magnetic particles are placed into a biologically-relevant substance collection well where the magnetic member is demagnetized so that the magnetic particles become free from the magnetic member and the electric interaction disappears to release the DNA from the magnetic particles. Thereafter, the magnetic particles are attracted and collected by the magnetic member, leaving DNA of interest in the well.

In this way, in one embodiment of the present invention, magnetic property is utilized to retain the trapping bodies on the carrier and the trapping bodies are charged to adsorb the biologically-relevant substance onto the trapping bodies. Therefore, a series of steps from the step of collecting the biologically-relevant substance from the gel to the step of analyzing the collected biologically-relevant substance can be automated.

2. Embodiments of the Present Invention

Hereinafter, embodiments of the present invention will be described in detail.

(1) Thin Tissue Section and Gel in which Biologically-Relevant Substance has Been Distributed Various gels are available for fractionating a biologically-relevant substance, and can be chosen in accordance with the purpose. Examples of a gel that can be used with the present invention include, but not limited to, agarose gel and polyacrylamide gel. A biologically-relevant substance can be distributed in a gel by usual electrophoresis or the like.

The present invention is also applicable to a thinly-sliced tissue section. For example, a collected thin tissue section can directly be sliced to obtain a slice or a thin tissue section can be frozen and sliced with a microtome or the like. Alternatively, a thin tissue section obtained by thinly slicing a tissue embedded in paraffin with a laser or a cutter can be mounted on a support and subjected to deparaffinization or the like to form a thin tissue section having the biologically-relevant substance distributed therein. The thus-formed thin tissue section can be placed in the above-described trapping device to acquire the biologically-relevant substance.

(2) Trapping Bodies and Carrier

Trapping bodies may be made of magnetic or conductive particles that can be charged upon trapping. Moreover, a substance having affinity for the biologically-relevant substance (for example, a probe that specifically bind with the biologically-relevant substance) may be attached around the trapping bodies. Examples of the trapping bodies include magnetic bodies that can be controlled with magnetic force and control objects that can be controlled by providing a probe. Preferably, the size of the magnetic bodies and the control objects is appropriately determined according to the fractionation pattern, and the shape thereof is preferably made into a particle or a stick form in terms of convenient handling. Any trapping bodies can be used as long as they can adsorb a biologically-relevant substance through electric interaction or affinity, and the shape and the material thereof are not particularly limited. Some of them will be exemplified below.

FIG. 1 shows illustrative drawings showing embodiments of trapping bodies.

Trapping bodies shown in FIG. 1(a) are made of magnetic particles or conductive particles that can be charged.

Although the material of the magnetic or conductive particles is not particularly limited, it is preferably made up of at least one of Fe, Co, Ni and the like. For example, a single body of any of Fe, Co or Ni, a Fe—Co alloy, a Fe—Ni alloy, or a ternary or quaternary alloy further added with a transition metal element such as Cr, Ti, Nb, Si or Zr can be used.

Furthermore, the above-mentioned magnetic particles may be covered with an inorganic material such as Ti, Al or Zr. Covering with any of these inorganic materials can, for example, enhance corrosion resistance or chemical stability.

The shape of the magnetic particles is not particularly limited, but it is preferably spherical in terms of easy handling. When they are formed into spherical shapes, the diameters thereof are preferably within a range of 0.1-100 μm.

Although the trapping bodies in the embodiment shown in FIG. 1(a) are retained on the carrier in a single layer, the number of layers is not limited thereto. When a magnetic member is used as the carrier to hold a plurality of magnetic particles, the magnetic particles randomly or in layers form a multi-layer structure (FIG. 1(b)).

In addition, according to the present invention, probes having affinity for the biologically-relevant substance (e.g., a nucleic acid or a protein) may be provided around the part of the spherically-formed magnetic particles (FIG. 1(c)). The trapping bodies shown in FIG. 1(c) are made up of spherically-formed particles and probes bound around these particles. Here, "having affinity" means that binding between the substances is enhanced such that they specifically bind to each other though chemical or physical interaction. Examples of a combination of substances having such affinity include an antigen and an antibody, a ligand and a receptor, and a nucleic acid (DNA or RNA) and a complementary strand thereof.

Binding of a substance having affinity for the trapping bodies utilizes specific binding, for example, between nucleic acid/complementary nucleic acid, receptor protein/ligand, enzyme/substrate, antibody/antigen, IgG/protein A, maltose-binding protein/maltose, polyhistidine peptide/metal ion such as nickel or cobalt, glutathione-S-transferase/glutathione, calmodulin/calmodulin-binding peptide, ATP-binding protein/ATP, streptavidin or avidin/biotin or enzyme/substrate. In order to allow these bindings, the surfaces of the particles are, for example, chemically treated to attach the substance having affinity for the biologically-relevant substance of interest onto the surfaces of the particles. Furthermore, a substance having affinity for a biologically-relevant substance of interest can be attached onto the trapping bodies, for example, through formation of a covalent bond such as amide bond, disulfide bond or thioether bond, or by utilizing specific interaction between streptavidin or avidin and biotin, hydrophobic interaction, interaction or polar interaction.

When the target of trapping is a protein such as an antigen, an antibody, a ligand or a receptor, for example, the above-described covalent bond may be utilized to provide particles bound with proteins (hereinafter, referred to as probe proteins) having affinity for the protein as the target for trapping. In forming this covalent bond, the functional group present in the probe protein is covalently bound to the surface of the particle to attach the probe protein onto the surface of the particle. Specific examples of a functional group that forms covalent bond include a carboxyl group, an amino group and a hydroxyl group. For example, in the case where a carboxyl group is provided on the surface of the particle, the carboxyl group is activated with a carbodiimide such as 1-ethyl-3-(3-dimethylaminopropyl)-3-ethylcarbodiimide hydrochloride (EDC) to allow reaction with an amino group present in the probe protein, thereby attaching the probe protein onto the particle surface by amide bond.

When the target of trapping is a nucleic acid such as DNA or RNA, for example, streptavidin or avidin/biotin interaction is utilized to provide particles attached with a complementary nucleic acid having affinity for a nucleic acid of interest. For example, biotin is introduced into a complementary nucleic acid while the particles are coated with avidin or streptavidin, thereby attaching the complementary nucleic acid to the particles.

The particles may be magnetic particles with paramagnetic property or metal particles that can be magnetized and demagnetized. Adsorption and release of the magnetic particles to and from the magnet are controlled with a magnet that is capable of controlling the magnetic property.

The structure of the carrier is not particularly limited as long as it can retain the trapping bodies, but it is preferably a magnetic member. Examples of such magnetic member include a magnet made of a ferromagnetic or soft magnetic material such as a permanent magnet or an electromagnet. It may also be a metal carrier that can be magnetized or demagnetized with a magnet or the like. The shape of the carrier is not limited and it may have a stick-like or pin-like shape (a polygonal column or a cylinder), a flat plate shape or a tapered shape. Although the carrier is connected to an electrode to charge the trapping bodies, a magnet may be covered with a conductive member as an intermediate member as described below, which may be connected to the electrode.

According to the present invention, a stick-like substrate can be used as a carrier as shown in FIG. 1(d) where the tip of the substrate is provided with trapping bodies. The upper end of the substrate may detachably be held by an arm. In this case, the carrier can be connected to an electrode so as to be charged.

FIG. 1(d) shows an example where probes as trapping bodies are directly bound to the carrier, where the carrier and the probes together serve as the trapping bodies (the carrier also serves as the trapping bodies).

Furthermore, according to the present invention, the shape of the carrier for retaining or securing the trapping bodies is not limited to a stick-like shape, and may be formed into a plate so that the opposing space between the carrier and, for example, the surface of a planar gel or a thin tissue section become constant (FIG. 1(e)).

(3) Collection of Biologically-Relevant Substance

Figure 2:
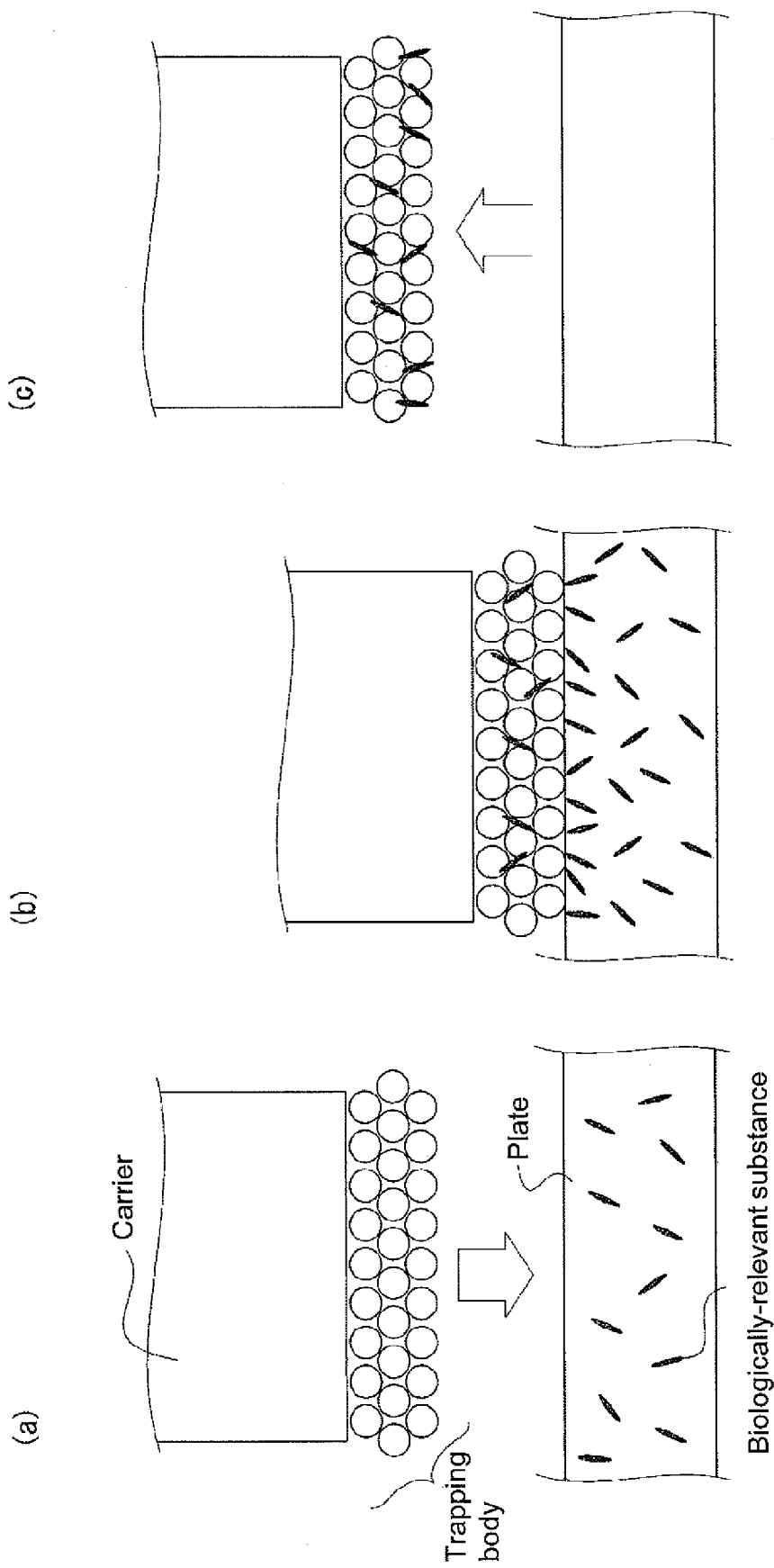
FIG. 2 Schematic views showing the principle of lifting up a biologically-relevant substance with the trapping bodies.

FIG. 2 shows views of an embodiment where a biologically-relevant substance is adsorbed by bringing trapping bodies (magnetic particles) retained by a carrier (magnet, etc.) into contact with a gel plate and charging the magnetic particles.

As can be appreciated from FIG. 2, when the magnetic particles make contact with a biologically-relevant substance fraction on a gel or a thin tissue section, the space between the magnetic particles is filled with water contained in the gel due to surface tension or capillary action. Owing to the electric interaction between the magnetic particles and the biologically-relevant substance, the biologically-relevant substance in the gel migrates toward the magnetic particles as the trapping bodies using water between the magnetic particles as a medium, where the biologically-relevant substance is adsorbed onto the magnetic particles to form a complex of the magnetic body and the biologically-relevant substance. In the case where the magnetic particles form a multi-layer structure, the biologically-relevant substance can be adsorbed onto the magnetic particles in a more steric manner (FIG. 2(b)). This phenomenon is based on the same principle as the behavior of the target of migration (DNA, protein, etc.) upon gel electrophoresis, where the electrode for charging the magnetic particles function as the electrode for electrophoresis while water and the magnetic particles function as the gel for electrophoresis (mesh structure).

After bringing the trapping bodies into contact with the surface of the gel or the thin tissue section, the trapping bodies are separated from the gel or the thin tissue section so as to lift up the biologically-relevant substance from the biologically-relevant substance fraction on the gel or the thin tissue section (FIG. 2(c)).

Figure 3:
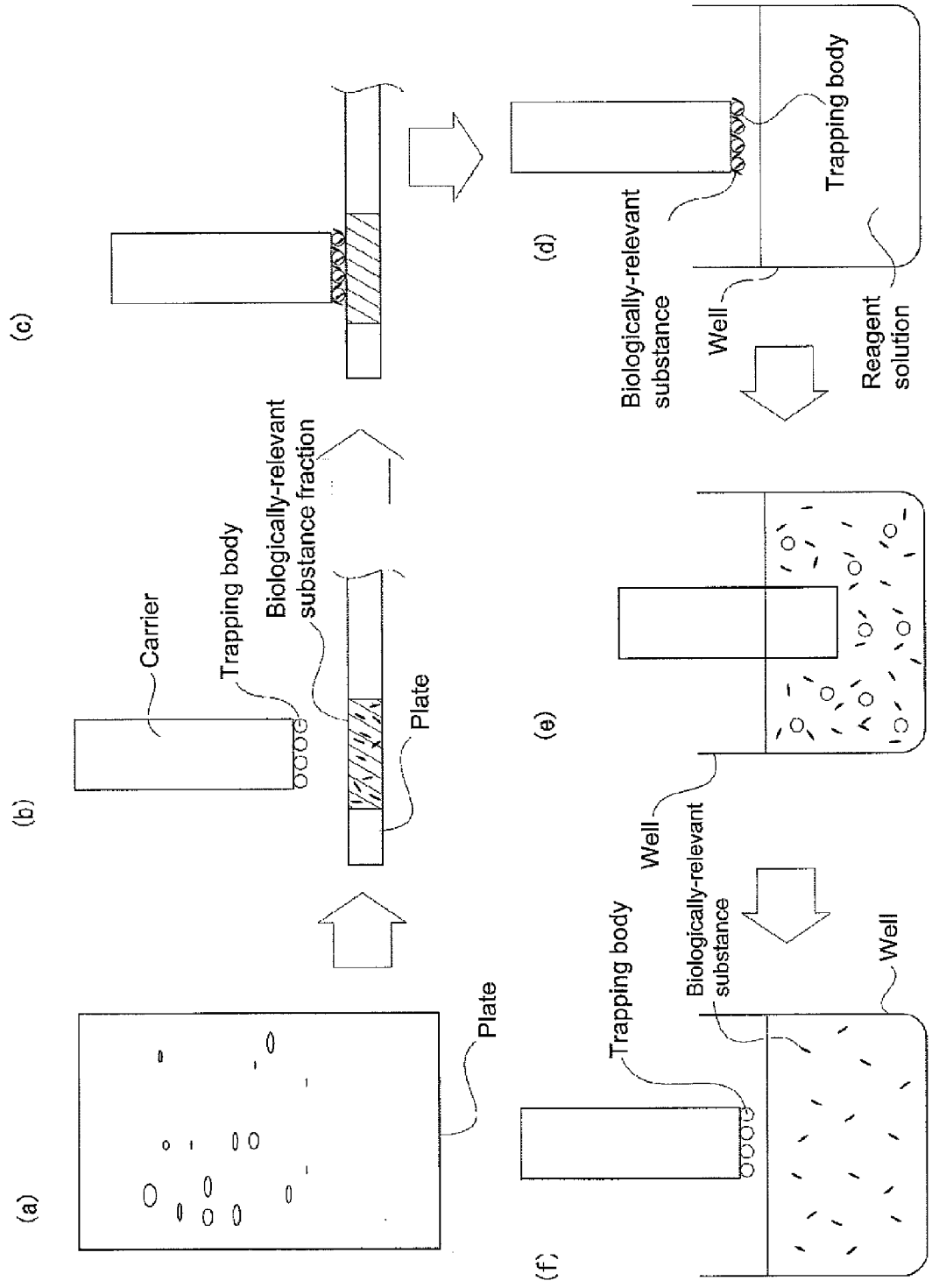
FIG. 3 Schematic views showing a process of collecting a biologically-relevant substance.

FIG. 3 shows drawings for illustrating general outline of a method for collecting a biologically-relevant substance from a gel fractionated by electrophoresis.

As shown in FIG. 3, the trapping bodies are positioned on the band of the gel plate (FIG. 3(a)) that has been subjected to electrophoresis and brought into contact with the electrophoresed fraction to charge the carrier (magnet) with the electrode so that the biologically-relevant substance is adsorbed onto the trapping bodies (FIGS. 3(b) and 3(c)). Subsequently, the trapping bodies are transferred to a reagent solution for demagnetization and discharge whereby the magnetic particles are released into the reagent solution while the biologically-relevant substance is separated from the magnetic particles (FIGS. 3(d) and 3(e)). Thereafter, the carrier is magnetized so that only the magnetic particles as the trapping bodies are attached to the carrier, thereby obtaining the biologically-relevant substance of interest in the well (FIG. 3(f)).

Figure 4:
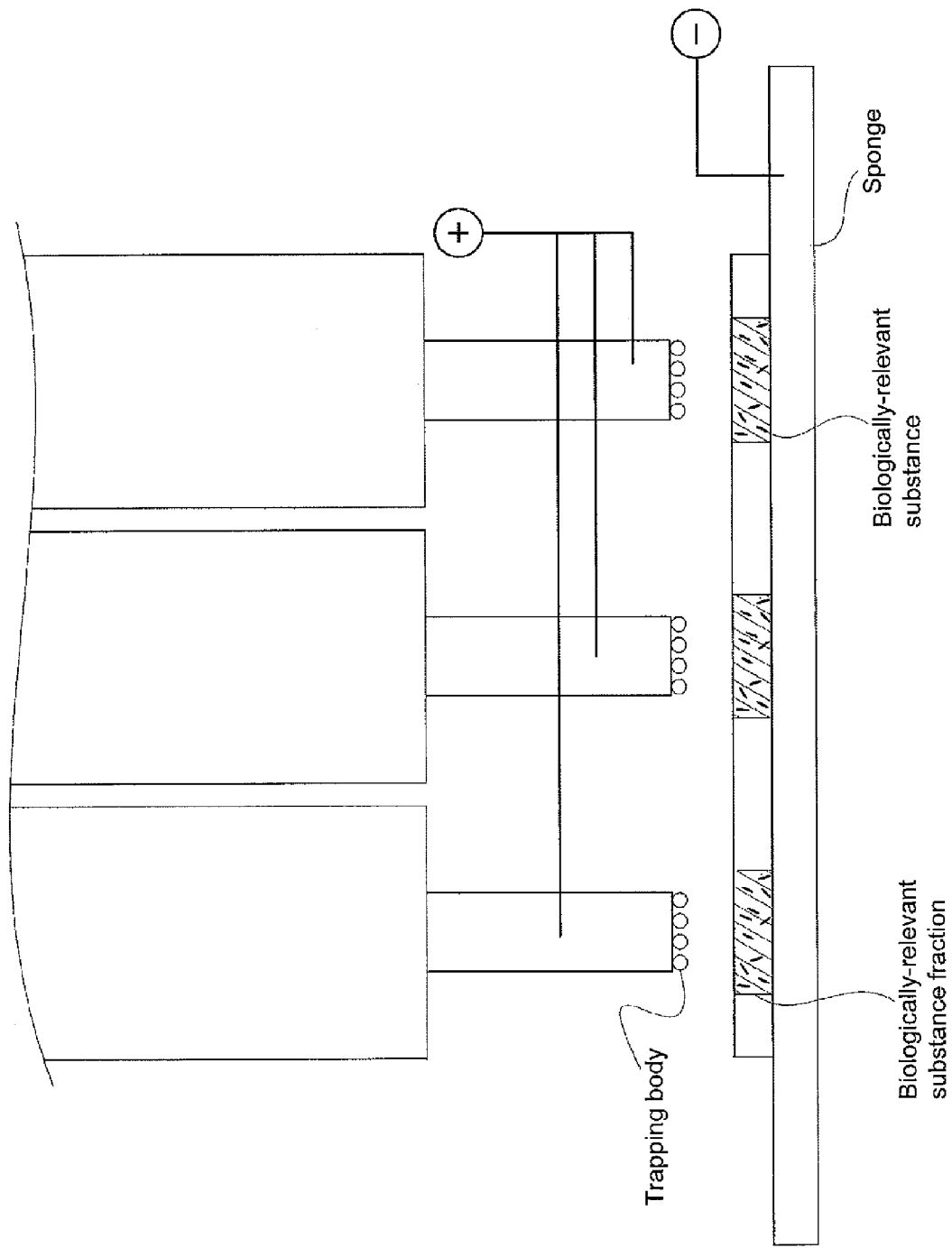
FIG. 4 A view showing one embodiment of a device of the present invention.

According to the present invention, an electric field for causing the biologically-relevant substance existing on the gel plate to move toward the trapping bodies is generated, for example, by providing a conductive member (electrode) that is capable of keeping moisture, for example, a sponge, beneath the gel plate (FIG. 4).

Once an electric field is generated between the electrode and the metal pin, the biologically-relevant substance moves toward the upper surface of the gel and is adsorbed onto the trapping bodies. Where a negatively-charged biologically-relevant substance is collected in such a manner, a negative electrode is provided beneath the gel plate and a metal pin that serves as a positive electrode above the gel plate to generate an electric field so that the negatively-charged biologically-relevant substance that has been fractionated in the gel plate 4 can efficiently be trapped with the trapping bodies.

A technique to remove the trapping bodies from the complex of the trapping bodies and the biologically-relevant substance is not limited to the above-described technique and other method can be used instead. For example, the trapping bodies can be released in the well to break the bond between the trapping bodies and the biologically-relevant substance. Then, the solution in the well can be passed through a filter that only passes the biologically-relevant substance, thereby acquiring the biologically-relevant substance.

In order to separate the biologically-relevant substance from a substance having affinity for the biologically-relevant substance, conditions that disrupt the interaction between the biological materials, for example, conditions that alter pH or salt concentration can be applied.

Figure 5:
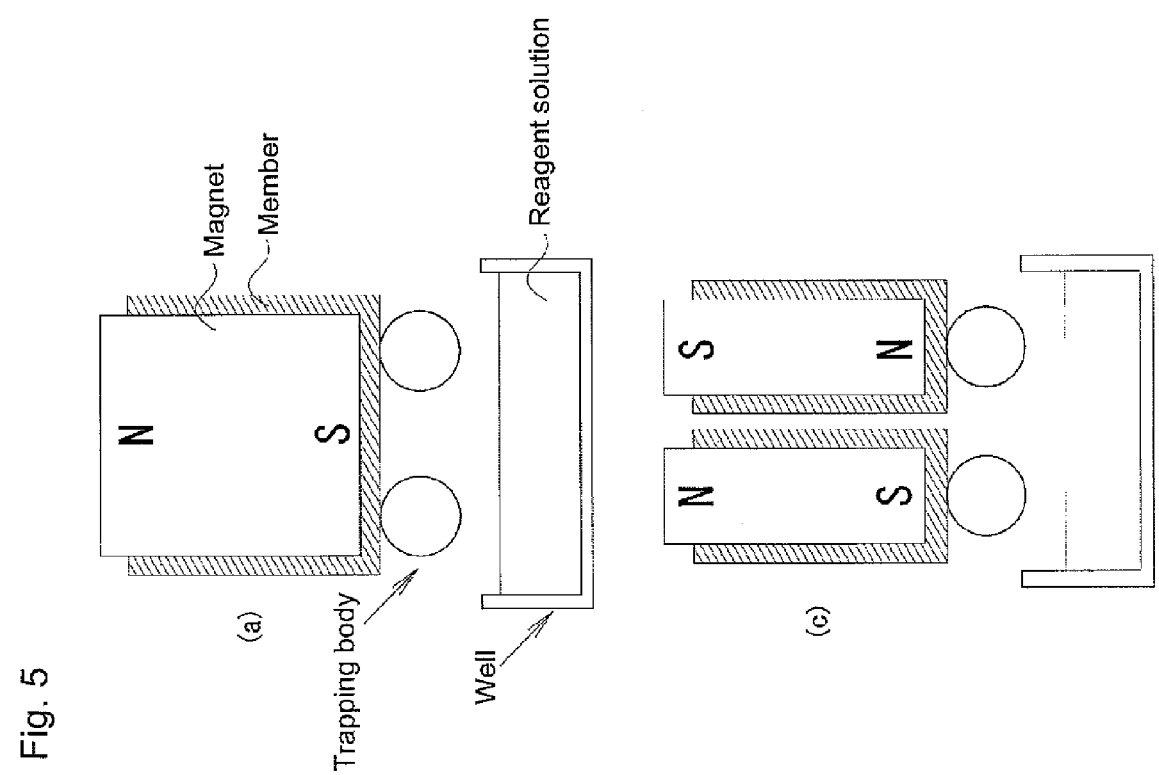
FIG. 5 Schematic views showing embodiments of combinations of a complex of the trapping bodies and the biologically-relevant substance and a well for receiving this complex.

FIG. 5 shows views showing embodiments of immersing the trapping bodies that have trapped a biologically-relevant substance in a well. Providing that a single unit refers to an embodiment where the trapping bodies (e.g., magnetic particles) are retained by a single carrier, embodiments may include: one where the trapping bodies of a single unit are immersed in one well (FIG. 5(a)); one where the trapping bodies of a single unit are immersed in two or more wells (FIG. 5(b)); and one where trapping bodies of two or more units are immersed in one well (FIG. 5(c)). In these units, a combination of the trapping bodies and an intermediate member can be used as a form of a carrier, where the trapping bodies can be retained with the magnet via this intermediate member. The intermediate member that separates the trapping bodies from the magnet retaining the trapping bodies serves as a cover for partitioning the magnet from the trapping bodies. Although it can be made from various materials, it needs to be a conductive member that is capable of being charged by the electrode. Such conductive member is preferably made of, for example, a carbon fiber material, copper or the like.

By providing a conductive member as described above where a permanent magnet is used to retain the trapping bodies, the permanent magnet can be moved up and down to retain the trapping bodies (magnetizing the trapping bodies) and release the trapping bodies (demagnetizing the trapping bodies) while the trapping bodies can be charged by the electrode via the conductive member to trap the biologically-relevant substance.

According to the present invention, a magnet for attracting the trapping bodies can be provided beneath the well so that the magnetic field of the magnet for adsorbing the trapping bodies and the magnetic field of the magnet beneath the well can be controlled to distribute the trapping bodies into multiple wells (FIG. 5(d)).

Although the trapping bodies can be controlled manually, they are preferably controlled automatically through a mechanical mechanism or an electric/electronic mechanism.

When the trapping bodies are to be controlled manually, the trapping device is provided, for example, with a jig that is capable of adsorbing/releasing the trapping bodies and trapping bodies for trapping a biologically-relevant substance from a gel in which the biologically-relevant substance has been fractionated or a thin tissue section containing the biologically-relevant substance, wherein the jig is manually operated so that the biologically-relevant substance is adsorbed onto the trapping bodies from the gel or the thin tissue section, and the trapping bodies adsorbing the biologically-relevant substance are collected.

In the case where the trapping bodies are to be automatically controlled, the trapping device can fractionate the whole gel into predetermined sections and then collect a biologically-relevant substance from that section. Alternatively, the trapping bodies may be positioned on a gel or a thin tissue section using coordinates so that a biologically-relevant substance can be collected from a position designated by the coordinates. Of course, the trapping bodies may be positioned on the gel or the thin tissue section by a technique other than the technique using coordinates.

As described above, the position where the trapping bodies make contact with may be determined on the gel or the thin tissue section by using coordinates, or the user can determine the position arbitrarily on the gel or the thin tissue section. Moreover, the position of the trapping bodies to make contact can be determined either manually or automatically.

Embodiments for designating the position on a gel or a thin tissue section for collecting a biologically-relevant substance are as follows.

i) In the case where the position of the trapping bodies to make contact is to be manually determined arbitrarily and visually by the user on a gel or a thin tissue section, for example, the user can bring the trapping bodies into contact with a biologically-relevant substance at the position of the band or the thin tissue section found out by staining or the like.

ii) In the case where the position of the trapping bodies to make contact is to be automatically determined on a gel or a thin tissue section, for example, a mechanism capable of tracing a position of a biologically-relevant substance found out by staining or the like based on color information can be utilized to determine the trapping position according to the type or shading of the color so that the trapping bodies can make contact with that position.

iii) In the case where the position of the trapping bodies to make contact is to be automatically determined by using coordinates, for example, an image of a thin tissue section or a gel in which a biologically-relevant substance has been fractionated can be taken and feature analysis is carried out for information of the taken image to calculate the position for acquiring the biologically-relevant substance, thereby determining the position of the trapping bodies to make contact. The image of the gel or the thin tissue section can be scanned with a line sensor or a picture of the whole plate can be taken with an image sensor.

iv) In the case where the position of the trapping bodies to make contact is to be manually determined by using coordinates, for example, an image of a thin tissue section or a gel in which a biologically-relevant substance has been fractionated can be taken, the position of acquiring the biologically-relevant substance designated by the user can be calculated on the taken image so as to determine the position of the trapping bodies to make contact on the gel or the thin tissue section.

A specific embodiment of a system of the present invention for obtaining a biologically-relevant substance from a thin tissue section or a gel in which the biologically-relevant substance has been distributed is, for example, provided with the following means:

(a) a position designating means for assigning the trapping bodies to a predetermined position or any of the segments that have been sectionalized into predetermined sections (for example, a matrix) on a thin tissue section or a gel in which the biologically-relevant substance has been distributed;

(b) a contact control means for bringing the trapping bodies into contact with the assigned position or segment; and (c) a collecting means for separating the biologically-relevant substance from the trapping bodies that made contact with the above-mentioned position or segment.

By providing the above-mentioned means, the device of the present invention can be automated. In this case, the device may further be provided with the followings.

(d) an image sensor for taking an image of a gel in which a biologically-relevant substance has been fractionated or a thin tissue section containing a biologically-relevant substance; and (e) a position designating means for designating the position for acquiring the biologically-relevant substance on the taken image.

Preferably, a thin tissue section or a gel in which a biologically-relevant substance has been distributed is formed into a plate.

For assignment in (a) above, another embodiment of the present invention can be provided with an image sensor for taking an image of the thin tissue section or the gel in which the biologically-relevant substance has been distributed; and a coordinates calculating means for figuring out coordinates on the gel or the thin tissue section corresponding to the position for acquiring the biologically-relevant substance determined from the image of the gel or the thin tissue section generated based on the image signal from the image sensor.

In addition, a contact control means for bringing the trapping bodies into contact with the coordinates figured out by the coordinates calculating means, and a collecting means for separating and collecting the biologically-relevant substance from the trapping bodies that made contact with the gel or the thin tissue section.

The acquisition position on the image of the gel or the thin tissue section generated based on the image signal may be determined automatically by applying an image processing technique, or with a pointing device that can be manipulated by the user such as a touch panel or a mouse.

Figure 6:
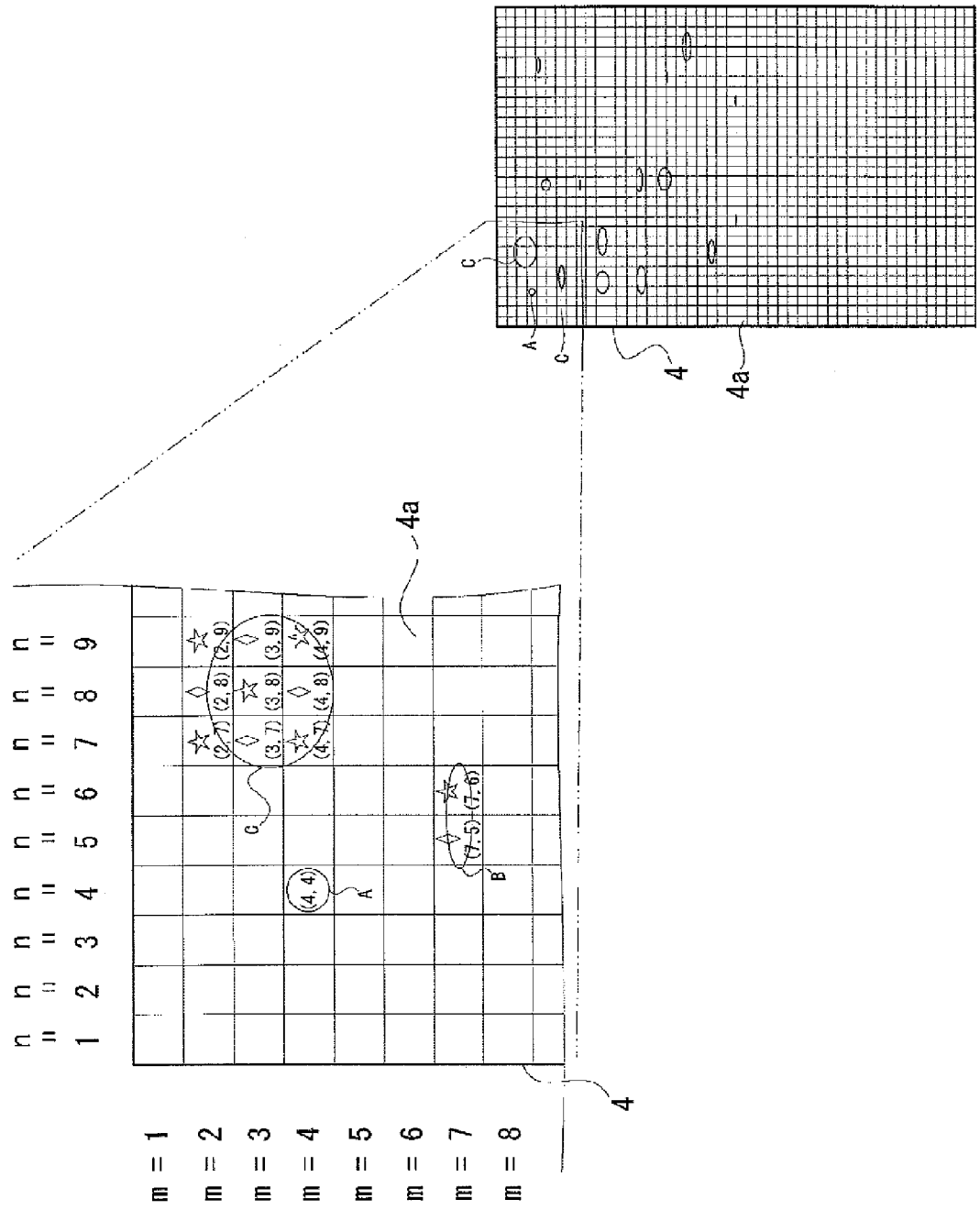
FIG. 6 A diagram for illustrating an embodiment of a sectionalized gel or thin tissue section.

FIG. 6 shows a diagram for illustrating an embodiment where the gel plate 4 is sectionalized into a matrix. By making a carrier to have a pin shape whose cross-sectional area at the tip is equal to or smaller than the section of the matrix or by making the section of the matrix equal to or larger than the cross-sectional area of the carrier with a pin-shaped tip, one carrier can be assigned to one matrix section so that a biologically-relevant substance contained in that section can be collected with the trapping bodies retained by the carrier.

Where the gel plate 4 is sectionalized into a matrix, and biologically-relevant substance fractions A, B and C are formed at predetermined positions on the gel plate 4 that has been sectionalized into a prescribed number of sections, segments 4a corresponding to these biologically-relevant substance fractions will be present. Pins (for example, soft magnetic metal pins) as carriers retaining magnetic particles will face the assigned segments 4a.

For example, the segment in the 4th row and 4th column (a segment in the "m"th row and "n"th column will be referred to as "segment (m,n)") corresponds to biologically-relevant substance fraction A, segments (7,5) and (7,6) correspond to biologically-relevant substance fraction B, and nine segments (2,7), (2,8), (2,9), (3,7), (3,8), (3,9), (4,7), (4,8) and (4,9) correspond to biologically-relevant substance fraction C (FIG. 6).

The number of sections in the matrix of the gel plate 4 is not limited and the gel plate may be sectionalized, for example, into 96 sections with 8 columns and 12 rows, 384 sections with 16 columns and 24 rows, 1536 sections with 32 columns and 48 rows. The number of sections may appropriately be altered according to the size of the biologically-relevant substance fractions on the gel plate 4. The sections that are subjected to collection may arbitrarily be determined and may be, for example, the whole gel plate or only a region where the biologically-relevant substance has been distributed. One or more pins are provided to be assigned to the segments 4a. When a single pin is provided, this pin retains and release the trapping bodies for collecting the biologically-relevant substance corresponding to all of the sections, and be in charge of collecting the biologically-relevant substance from all of these sections. When a plurality of pins are provided, the number of the pins provided may correspond to the number of the entire sections or may be any number, for example, the number of sections in one row or one column.

The tip of each pin detachably adsorbs the trapping bodies, where the trapping bodies are, for example, magnetic particles or magnetic particles having probes provided around them. Thus, trapping bodies can be assigned to each of the segments 4a. The size of the gel plate 4 is, for example, 12 cm by 9 cm, which is sectionalized into 1536 segments with 32 columns and 48 rows and thus 1536 soft magnetic metal pins 20 can be arranged to correspond to these segments 4a at intervals of 2.25 mm (at a pitch of 2.25 mm).

When the positions for acquiring the biologically-relevant substance determined by the user has a plurality of segments, the activation pattern of the metal pins is preferably determined such that the interaction between the adjacent trapping bodies is as small as possible.

For example, since fraction B in FIG. 6 has segments (7,5) and (7,6), either one of pins (7,5) and (7,6) may be descended first and the other later or both of them may be descended at the same time to acquire the biologically-relevant substance fraction B. Specifically, with respect to biologically-relevant substance fraction B, for example, either the metal pin corresponding to segment 4a indicated by diamond mark or the metal pin corresponding to segment 4a indicated by the star mark may be activated one after the other. By activating the pins (7,5) and (7,6) one after the other, magnetic interference to the adjacent magnetic particles can be minimized.

Similarly, since fraction C extends over nine segments (2,7), (2,8), (2,9), (3,7), (3,8), (3,9), (4,7), (4,8) and (4,9), nine metal pins (2,7), (2,8), (2,9), (3,7), (3,8), (3,9), (4,7), (4,8) and (4,9) need to be descended to make contact with fraction C to acquire a biologically-relevant substance from fraction C. Alternatively, metal pins less than the number of the segments (for example, one or two metal pins) may be used for collecting the biologically-relevant substance from the respective segments.

In this case, in the same manner as fraction B above, either the metal pin corresponding to segment 4a indicated by the diamond mark or the metal pin corresponding to segment 4a indicated by the star mark may be activated first and the other later. By intermittently descending the metal pins in this way, mutual magnetic interference between the adjacent trapping bodies can be minimized. In addition, generation of undesirable electric field between the electrodes corresponding to the adjacent metal pins can also be prevented.

According to the present invention, an embodiment of activating the metal pin is not limited to the above-described embodiment and appropriate variation is possible. For example, an activation pattern for the metal pins to make contact with the biologically-relevant substance fraction may be determined not only for the metal pins adjacent in the longitudinal or horizontal direction but also those adjacent in diagonal direction.

Figure 7:
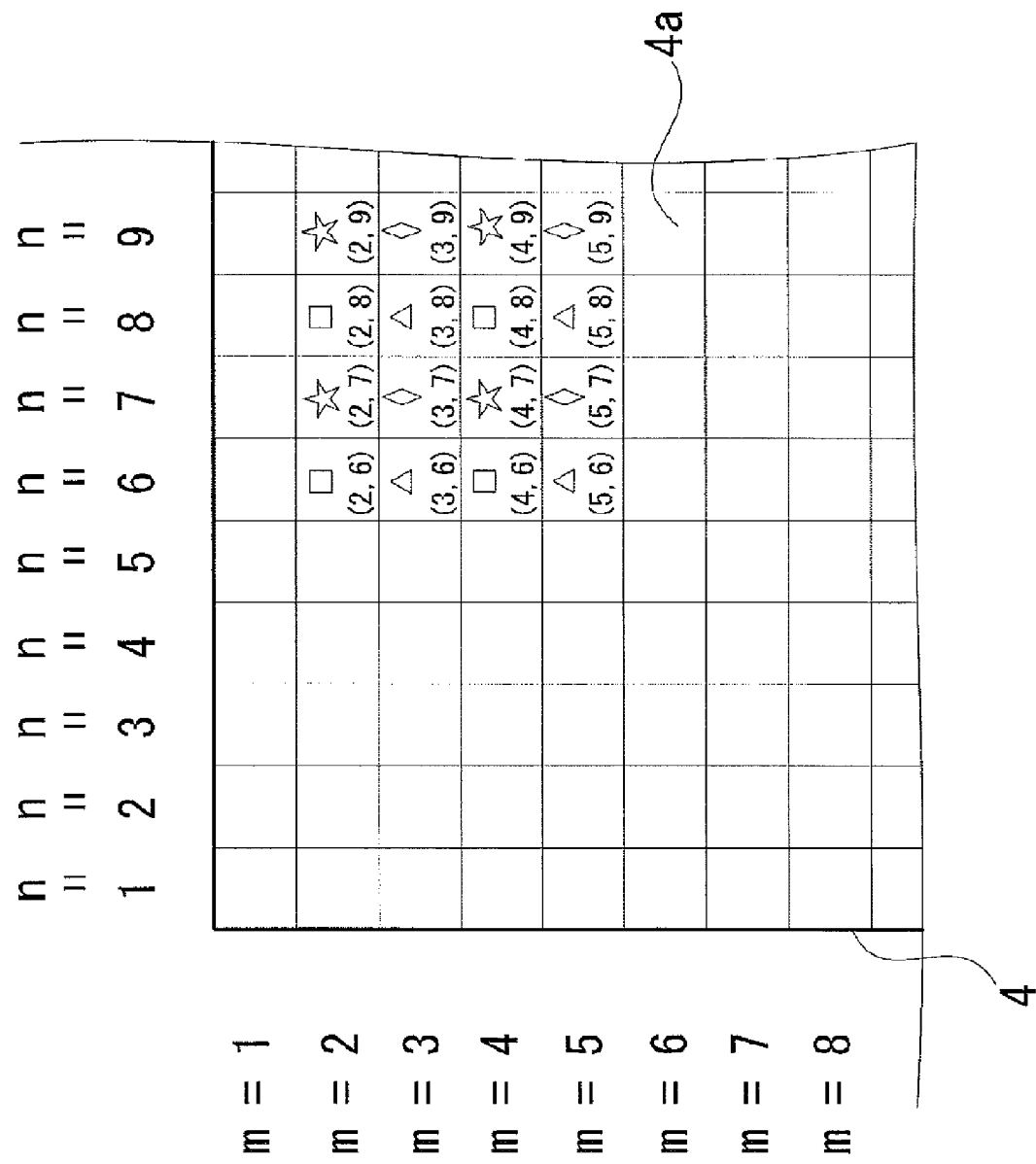
FIG. 7 A diagram for illustrating an embodiment of a sectionalized gel or thin tissue section.

When the biologically-relevant substance in the region shown in FIG. 7 is to be collected, the metal pins may be activated in multi-steps by first activating the metal pins corresponding to segments 4a indicated by the square mark and then the metal pins corresponding to segments 4a indicated by the star mark, the diamond mark and finally the triangle mark in this order (in four steps in this embodiment). For example, groups of segments corresponding to each mark may be produced so as to activate the pins for individual group. Activation of the pins belonging to each group may be carried out simultaneously or separately. In this way, a plurality of metal pins can be grouped upon activation so that the activated metal pins are separated from each other to some extent while the number of activation steps can be increased to further reduce the mutual interference between the metal pins.

Figure 8:
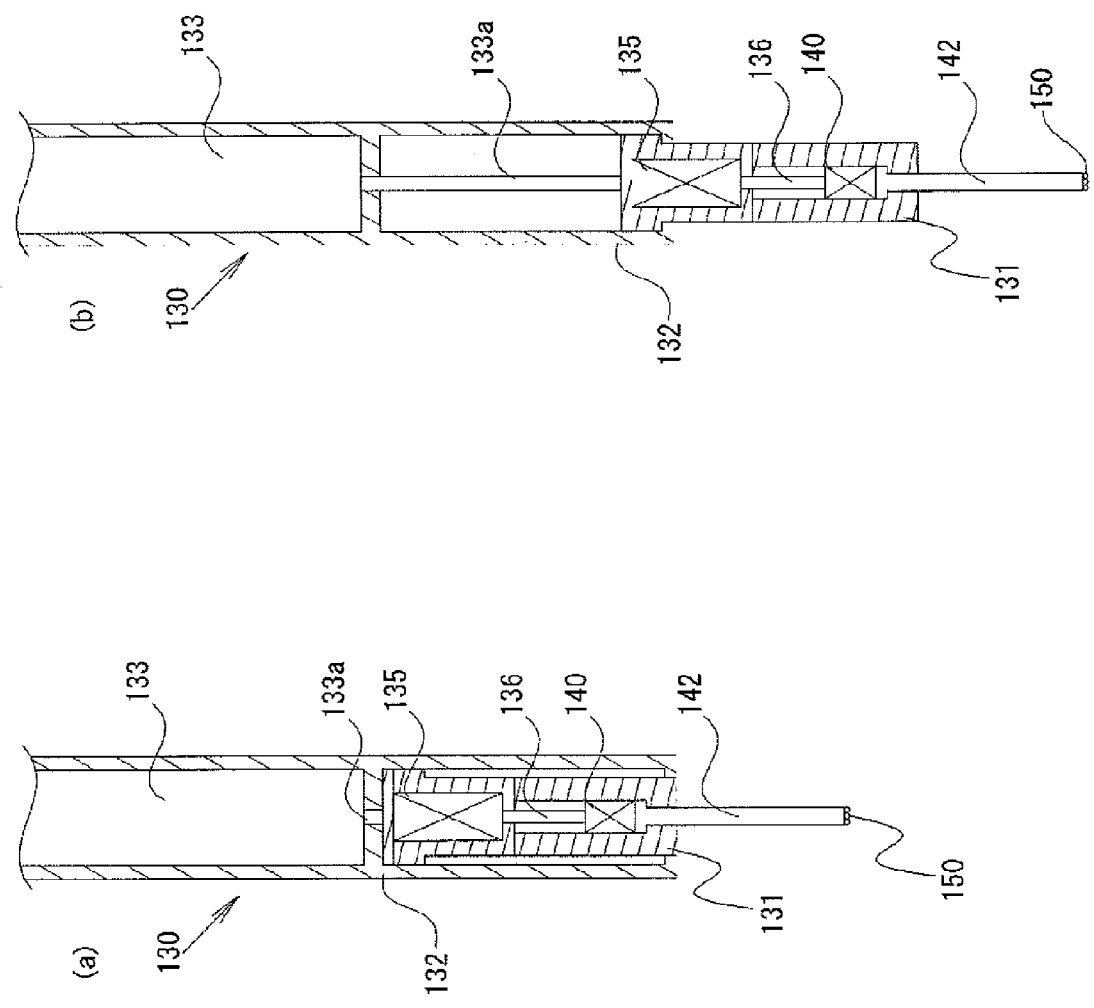
FIG. 8 Partial cross-sectional views of an adsorption mechanism partially cut along the plane parallel to the extending direction of the metal pin.

An exemplary embodiment of the present invention where a soft magnetic metal pin is used as a carrier for retaining the trapping bodies for a biologically-relevant substance is shown in FIG. 8. FIG. 8 is a partial cross-sectional view of an adsorption mechanism provided with a soft magnetic metal pin, partially cut along the plane parallel to the extending direction of the adsorption mechanism. As can be appreciated from FIG. 8, the structure of the adsorption mechanism 130 comprises a first housing 131, a second housing 132, a magnet 140, a soft magnetic metal pin 142 and else.

The soft magnetic metal pin 142 has the role as a carrier for retaining the trapping bodies, and held by the first housing 131 which is, in turn, held by the second housing 132. The magnet 140 is provided in the first housing 131 such that it is movable between the contact position where it hits the soft magnetic metal pin 142 and the setback position where it is separated away from the soft magnetic metal pin 142 so as not to make contact. Due to the movement of this magnet 140, the magnetic property of the soft magnetic metal pin 142 can be controlled. Examples of the soft magnetic metal include pure iron, a Fe—Ni alloy, a Fe—Si alloy and a Fe—Co alloy, which may appropriately be selected and used. The shape of the pin may be cylindrical, prismatic or tapered, which may appropriately be changed according to the purpose.

The magnet 140 is connected to, for example, a plunger 136 whose protrusion and retraction are controlled by a solenoid 135. When the plunger 136 is protruding, the magnet 140 stays at the contact position where the soft magnetic metal pin 142 is magnetized to function as a magnet, whereas when the plunger 136 is retracted, the magnet 140 stays at the setback position where the soft magnetic metal pin 142 is demagnetized and lose the function as a magnet.

The soft magnetic metal pin 142 is connected to an electrode (positive electrode) so that when a voltage is applied between this electrode and the other electrode (negative electrode (for example, a water-containing sponge)) (see FIG. 4), an electric field is generated between the electrode and the soft magnetic metal pin 142. Trapping bodies 150 are releasably adsorbed onto the tip of the soft magnetic metal pin 142, and the biologically-relevant substance that has migrated to the surface of the gel plate binds with the trapping bodies 150 at the tip of the soft magnetic metal pin 142 to form a complex. The electrode may be connected via the first metal housing 131.

Figure 9:
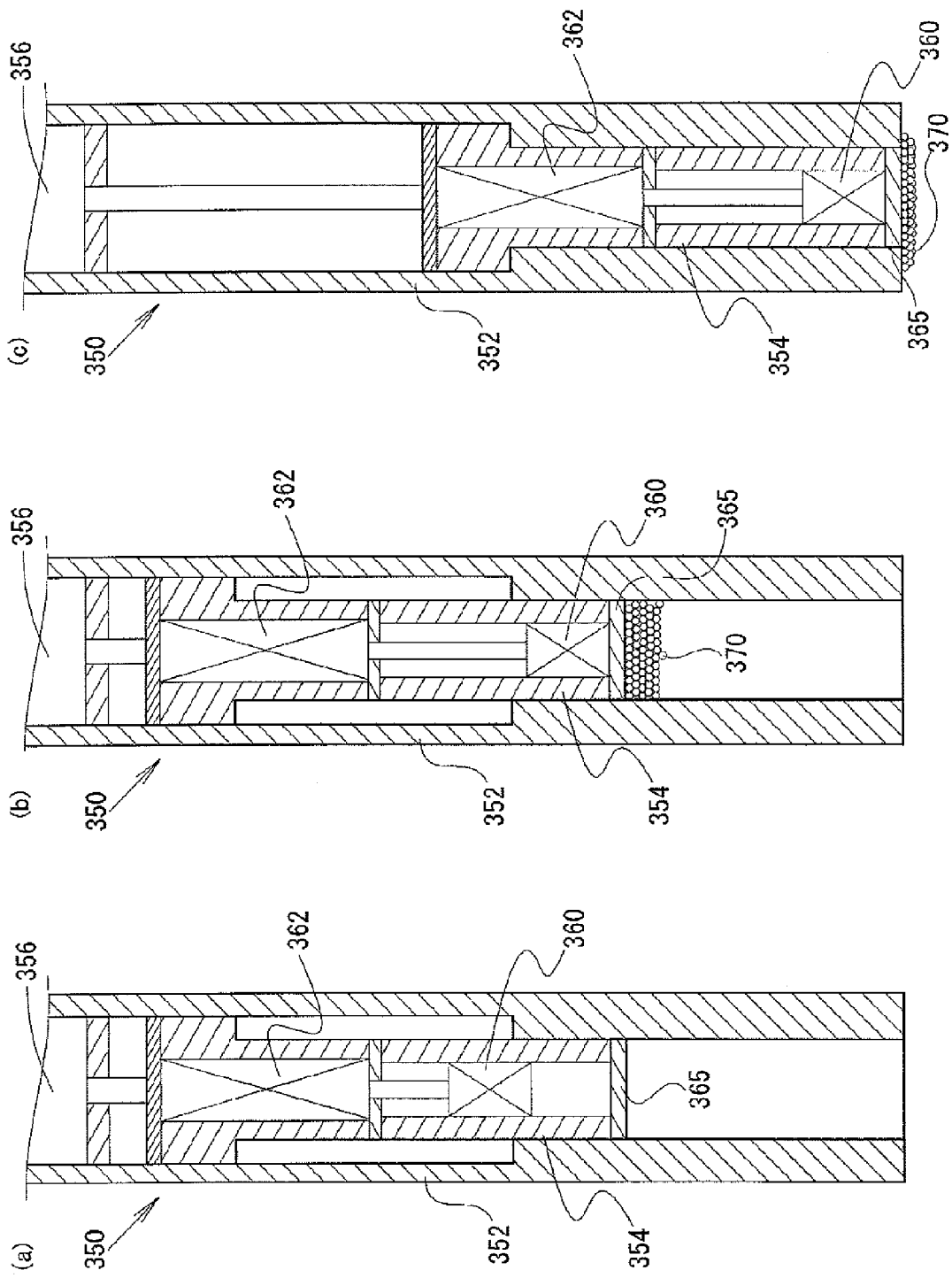
FIG. 9 Cross-sectional views of an adsorption mechanism constructed to house the trapping bodies, cut along the longitudinal direction of the housing.

The embodiment of the adsorption mechanism is not limited to the above-described example. For example, it may be an embodiment where the trapping bodies are suctioned/discharged inside and outside the adsorption mechanism as shown in FIG. 9. For example, as shown in FIG. 9(a), the adsorption mechanism 350 is provided with a housing 352 and a magnet device 354. The housing 352 is formed into a generally cylindrical shape, while the magnet device 354 is movably provided inside the housing 352. The magnet device 354 is connected to an electrode. An adsorption plate 365 is movably provided between the deployment position where it is positioned at the open end at the tip of the housing 352 and the retraction position where it is drawn within the housing 352. The movement of the magnet device 354 is controlled, for example, by an actuator 356 placed in the housing 352. The magnet device 354 may be provided with a magnet 360 and a solenoid 362, where the magnet 360 is movably provided between the contact position where it hits the adsorption plate 365 and the setback position where it is drawn away from the contact position to the solenoid side.

As shown in FIG. 9(b), when the magnet 360 is at the contact position, the adsorption plate 365 can adsorb the trapping bodies 370 while when the magnet 360 is at the setback position, the adsorption plate 365 cannot adsorb and thus release the trapping bodies 370.

As shown in FIG. 9(c), in order to capture a biologically-relevant substance, the magnet device 354 is controlled to stay at the deployment position. Once the magnet device 354 is placed at the deployment position, the trapping bodies 370 are deployed at the tip of the adsorption mechanism 350. The trapping bodies 370 can adsorb the biologically-relevant substance on a gel plate once they are charged by the electrode connected to the magnet 360.

As a mechanism for controlling the movement of the trapping bodies having a magnetic property, the strength of the magnetic field may be adjusted by controlling the position of the permanent magnet as described above. Alternatively, a current supplied to the electromagnet may be modulated to adjust the strength of the magnetic field to control the movement of the trapping bodies. Here, an adsorption mechanism will be illustrated which adjusts the strength of the magnetic field by modulating the current supplied to the electromagnet and which distributes the trapping bodies into multiple wells with a pumping mechanism.

When the movement of the trapping bodies having a magnetic property, for example, magnetic particles, needs to be controlled in a more smooth manner, the trapping bodies may be combined with a liquid vehicle such as water to produce a fluid. The produced fluid can be discharged/suctioned using a microminiature pump that makes use of a piezoelectric element such as a piezo element or a SMA (shape-memory alloy) to control the movement of the trapping bodies.

Figure 10:
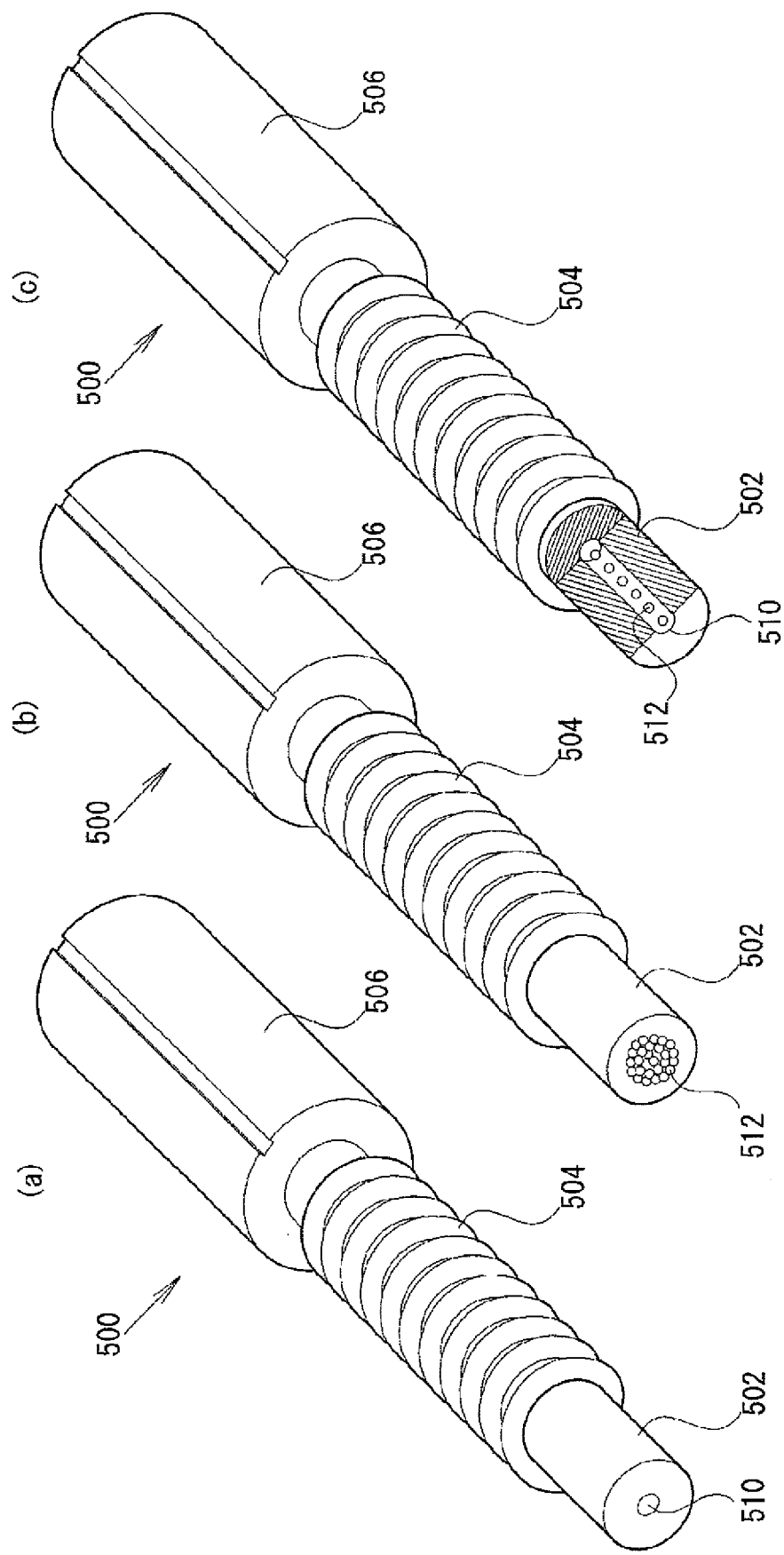
FIG. 10 Perspective views and a perspective cross-sectional view showing a structure and an embodiment of activation of the adsorption mechanism which is capable of adsorbing a magnetic body and drawing a fluid.

For example, as shown in FIG. 10, the adsorption mechanism 500 comprises a soft magnetic metal pin 502, a coil 504, a microminiature pump (micropump) 506, a piezoelectric element or actuator (not shown) for descending and ascending the adsorption mechanism, and the like. The soft magnetic metal pin 502 is formed into an elongated tube and connected to an electrode. In addition, the end of the soft magnetic metal pin 502 is provided with the microminiature pump 506. The coil 504 is wound on the soft magnetic metal pin 502 so that the soft magnetic metal pin 502 is activated as a magnet when a current flows though the coil 504.

One end of the soft magnetic metal pin 502 is provided with an aperture 510 for discharging/suctioning the trapping bodies. This aperture 510 is in communication with the microminiature pump 506 arranged on the opposite end of the soft magnetic metal pin 502. The diameter of the aperture 510 is set to, for example, several-tens of urn to several-hundreds of µm. The trapping bodies go in and out through this aperture 510.

The microminiature pump 506 comprises, for example, a cylinder, a piston arranged in the cylinder and a piezoelectric element for driving the piston. An example of a piezoelectric element includes a piezo element. A current flowing through such a piezoelectric element can be modulated to control the driving of the piston.

In this manner, the trapping bodies 512 are fluidized to be controlled by the microminiature pump so that a predetermined amount of trapping bodies can be distributed among a plurality of wells.

Although a trapping device comprising a single adsorption mechanism 130 has been illustrated in the above-described embodiment, a plurality of adsorption mechanisms may be provided. The number of the adsorption mechanisms may be determined (for example, five or ten) according to the number of fractions collected in a single process (for example, a single row) so that the biologically-relevant substance can efficiently be lifted up from the biologically-relevant substance fraction on the gel plate.

In one embodiment of the present invention, a position where the trapping bodies make contact on the gel plate is predetermined and the trapping bodies are brought into contact with the gel plate at this predetermined position. The position on the gel plate may be determined automatically, manually or both.

When the position for acquiring the biologically-relevant substance is automatically determined to bring the magnetic particles into contact with the gel plate at that position, for example, the plate image is analyzed to identify the biologically-relevant substance fraction to figure out the coordinates on the gel plate corresponding to this identified fraction. Then, the trapping bodies are moved to the segment including the figured out coordinates to activate the assigned magnetic particles.

In the above-described embodiment, the magnetic property of the soft magnetic metal pin is controlled by moving the magnet closer to or away from the soft magnetic metal pin to control the movement of the magnetic particles. The movement of the magnetic particles may alternatively be controlled by using, for example, an electromagnet made with a stick-shaped iron core wound with a coil. By using an electromagnet, a solenoid and a plunger can be omitted and hence the device can be downsized.

(4) Scaling Up and Scaling Down Sections Subjected to Collection

Although the trapping device according to the present invention may be provided with the same number of wells as the segments on the gel plate, the trapping device may alternatively be provided with wells corresponding to some of the segments on the gel plates. By doing so, a biologically-relevant substance can be collected from a part of the region in a larger scale.

Figure 11:
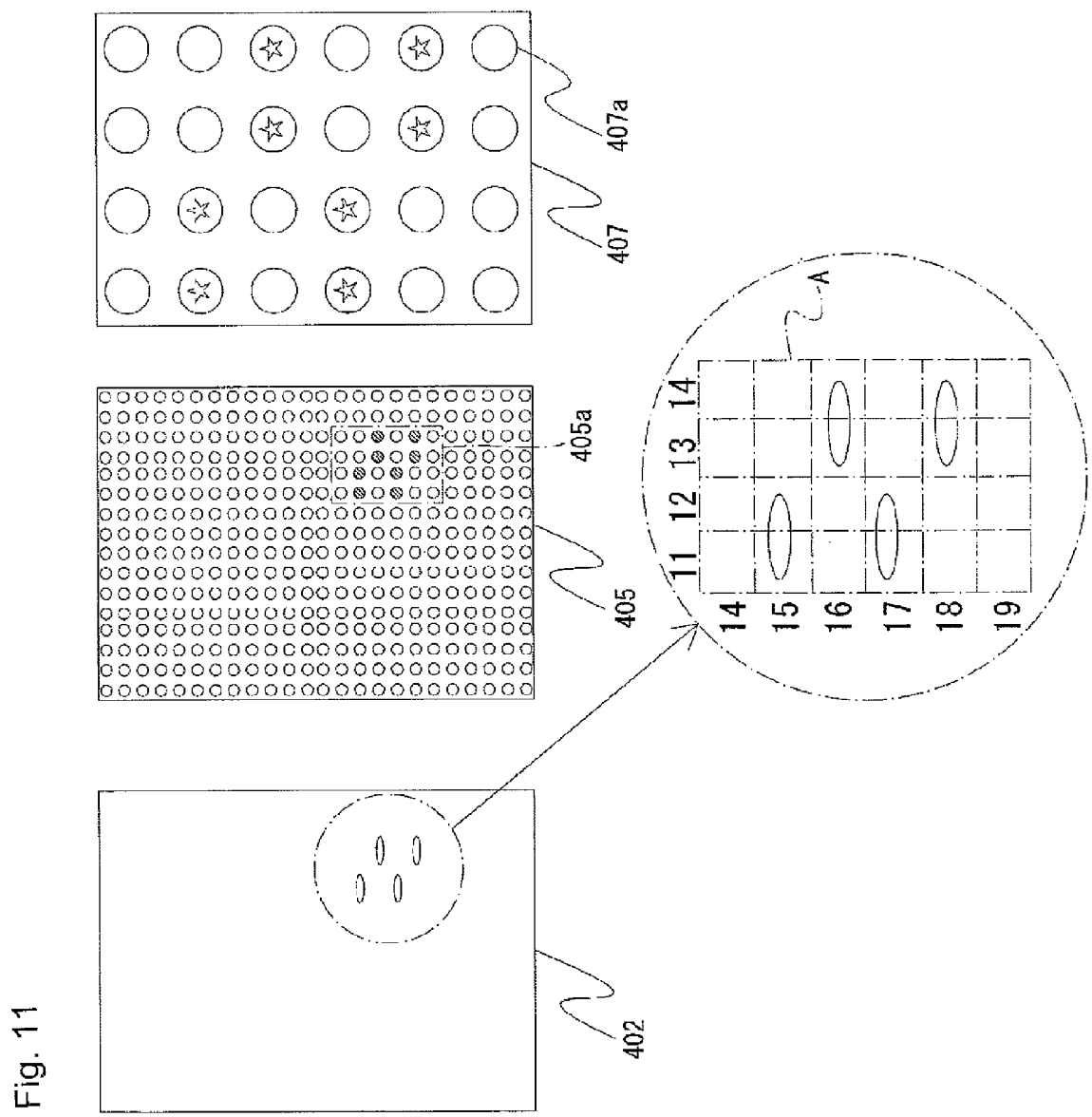
FIG. 11 Drawings showing a gel plate, a first well plate and a second well plate where a content in the wells corresponding to a part of the segment is scaled up.

FIG. 11 illustrates an outline of a case where a biologically-relevant substance is collected from a part of the segments on the gel plate in a larger scale.

As shown in FIG. 11, the gel plate 402 is segmented, for example, into 24 rows and 16 columns and the biologically-relevant substance is collected in a first well plate 405 having 24×16 wells by using an adsorption mechanism compatible with these segments.

Among these 24×16 wells of the first well plate 405, if the content in a well section 405a having, for example, 6 rows and 4 columns of wells is to be scaled up, the content in each of the wells in the well section 405a is transferred to a second well plate 407 having 6×4 wells with larger volumes.

By transferring the contents in the wells of the well section 405a to the scaled-up wells 407a of the second well plate 407, for example, the biologically-relevant substance can be adapted to culture and thus the biologically-relevant substance of interest can be obtained in a larger scale.

If the second well plate having the same occupying size as the first well plate is to be constructed, the center-to-center spacing (pitch) of the wells of the second well plate is made larger than that of the first well plate so that, for example, the biologically-relevant substance in the wells of the second well plate can be obtained manually and directly by the user using a pipette.

Moreover, according to the present invention, multiple sets of reduced-size well group corresponding to the whole area of the gel plate are provided so as to obtain multiple sets of biologically-relevant substance on the gel plate in a smaller scale.

Figure 12:
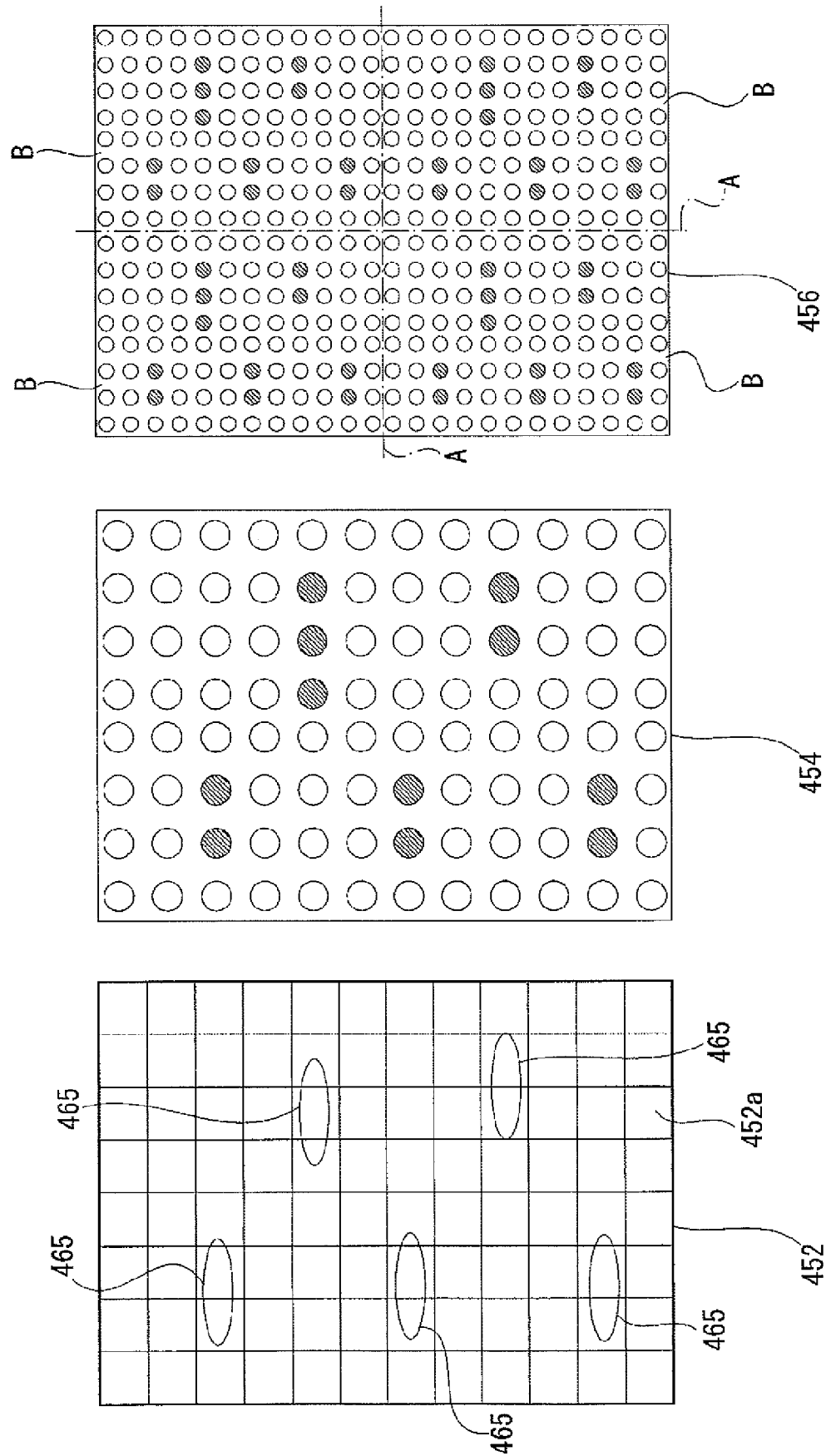
FIG. 12 Drawings showing a gel plate, a first well plate and a second well plate where a content in the wells corresponding to a part of the segment is scaled down.

FIG. 12 illustrates an outline of a case where the biologically-relevant substance on the gel plate is scaled down and obtained in multiple sets. As shown in FIG. 12, the gel plate 452 is segmented, for example, into 12 rows and 8 columns and the biologically-relevant substance 465 fractionated on the gel plate 452 is collected in a first well plate 454 having 12×8 wells by using an adsorption mechanism compatible with these segments.

The content in the first well plate 454 is transferred into a plate having further scaled-down wells (for example, a second well plate 456 having 24×16 wells).

In the above-described example, the number of the wells of the second well plate 456 is four times the number of the wells of the first well plate 454. Therefore, by repeating the action of transferring the content of the first well plate 454 into one-quarter area of the second well plate 456 for four times, up to four sets of the content of the first well plate 454 can be obtained on the second well plate 456 in a smaller scale.

If the number of sets of the content collected in the first well plate needs to be increased, for example, to 6 or 8 sets, the number of the wells of the second well plate can be increased.

If the second well plate having the same section number as the first well plate is to be constructed, the center-to-center spacing (pitch) of the wells of the second well plate is made smaller than that of the first well plate so that the trapping device can avoid from getting larger while different kinds of tests can be conducted on the obtained biologically-relevant substance.

EXAMPLES

Objective

Figure 13:
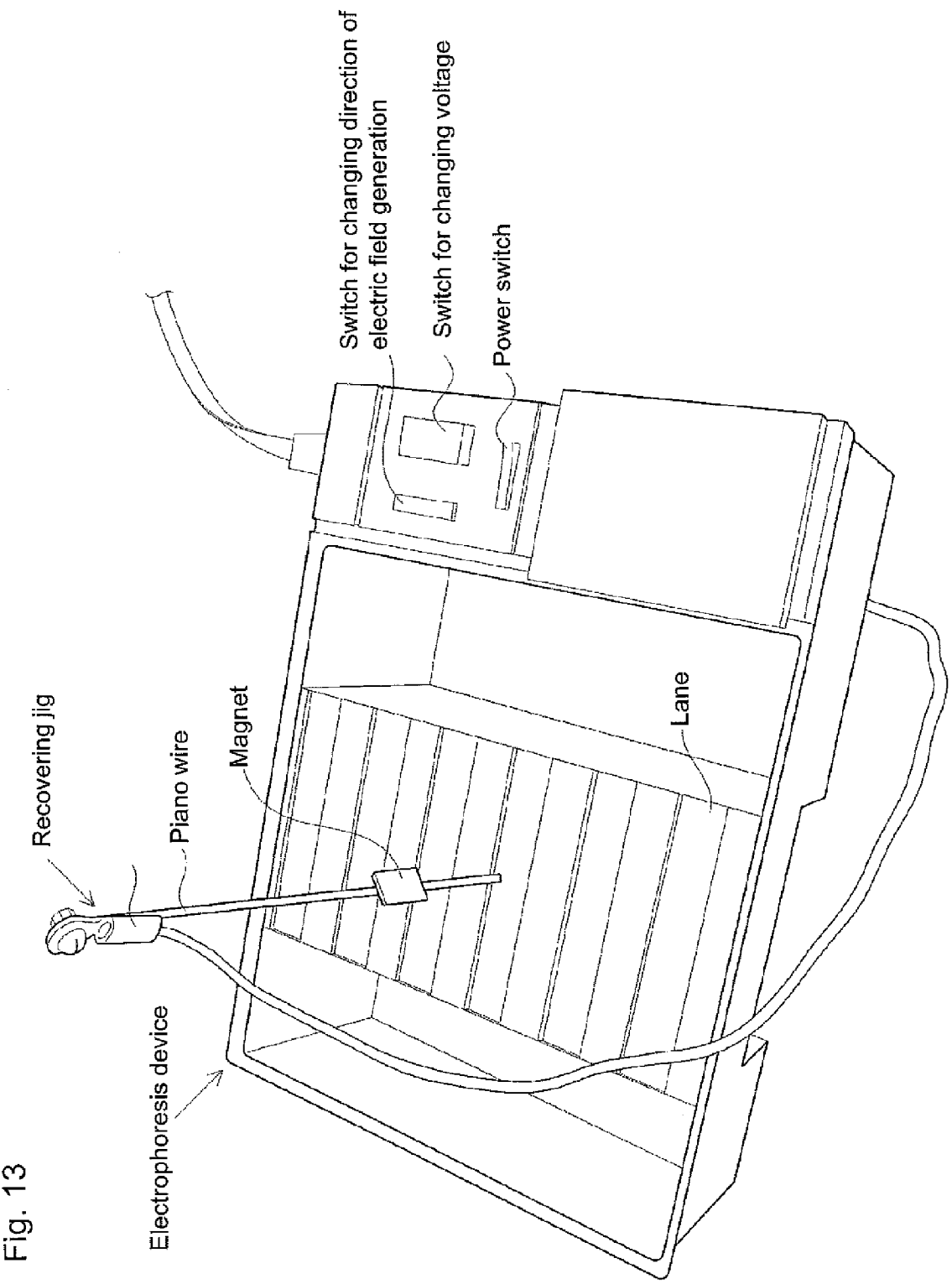
FIG. 13 A perspective view showing an electrophoresis device and a recovery jig.

Collection of a biologically-relevant substance by using a trapping device of the present invention will be verified.
Equipments and Sample Used
Electrophoresis Device and Recovery Jig (See FIG. 13)
Experimental Gel
An experimental gel was prepared under the following conditions.
Electrophoresis gel: 1% agarose gel (thickness 2-3 mm)
Electrophoresis sample: two types of DNA markers (λDNA/Hind III Marker, WideRange), Human Genome, PCR products (1038 bp)
Description of Electrophoresis Device and Recovery Jig
As shown in FIG. 13, a submarine electrophoresis device was used for performing electrophoresis while keeping the agarose gel submerged in a buffer. The electrophoresis device is provided, on the right hand side in FIG. 13, with a power switch, a switch for changing the voltage between 100V and 50V and a switch for changing the direction of electric field generation as well as first to sixth electrophoresis lanes in the central area of the device.

The recovery jig used had an electrode (for example, a positive electrode) on one end of a piano wire magnetized with a magnet, and permalloy powder made of a Ni—Fe alloy (50% Ni—Fe PF-20F) adsorbed on the other end.

Procedure
1. The followings were pipetted into the first to sixth lanes to perform electrophoresis at 100V for 30 minutes.

M1: molecular weight marker 1 (λ, DNA/Hind III Marker);
HG: Control Human Genome DNA (Roche);
PCR: PCR product (1038 bp); and
M2: molecular weight marker 2 (Wide-Range DNA Ladder).

Figure 14:
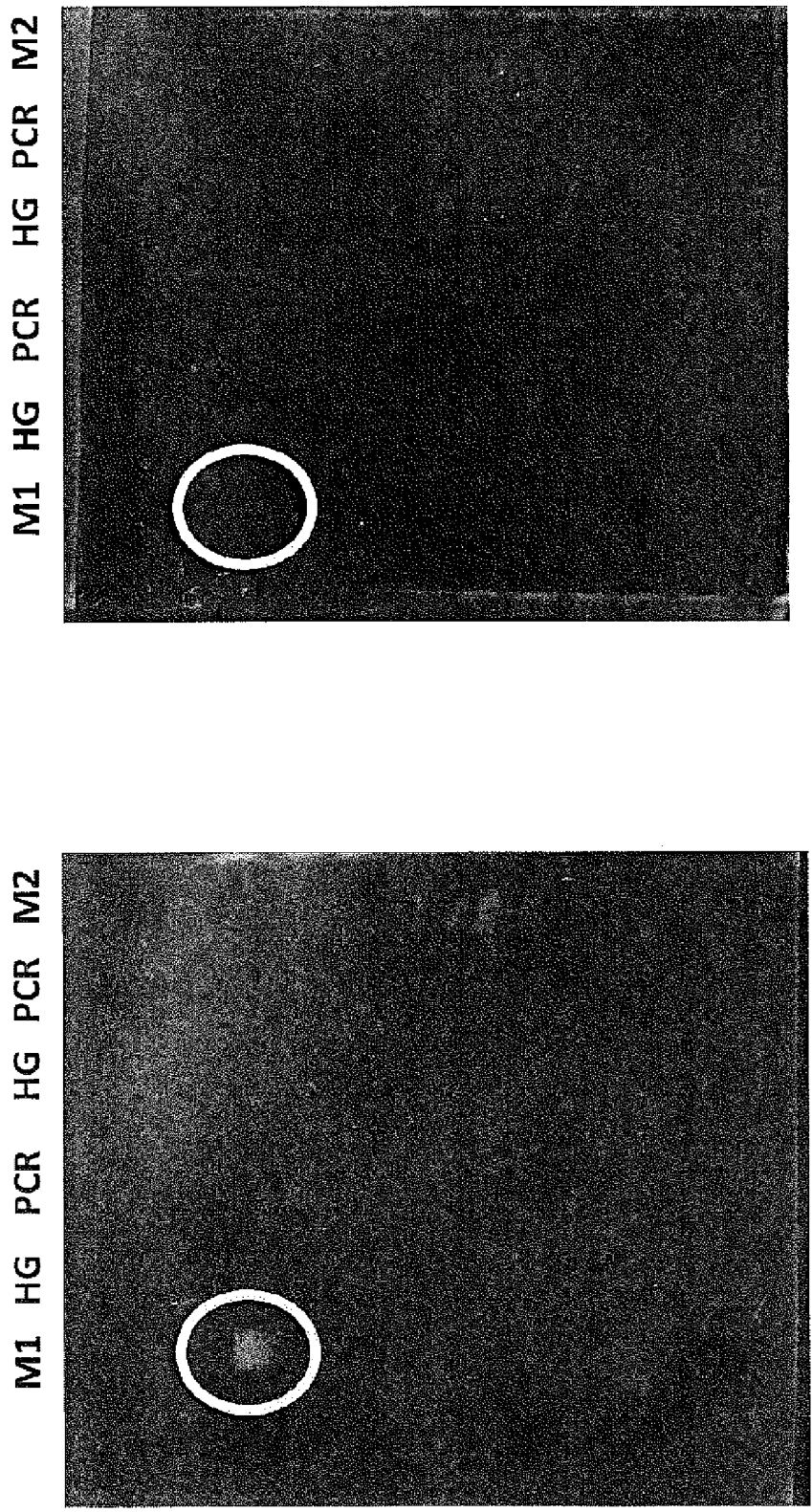
FIG. 14 UV fluorography images of a gel after electrophoresis and the gel after recovering a nucleic acid.

2. The electrophoresed gel was stained with ethidium bromide, washed and then subjected to UV photography to confirm the location of the sample.
3. The tip of the recover jig having permalloy powder adsorbed thereon was placed on the confirmed location of the nucleic acid appearing as a white band (encircled)) in lane M1 (FIG. 14, left panel) and pressed on the gel for 150 seconds while applying a voltage of 100V.

Results

Following the collection process, the gel was confirmed again by UV photography. As can be appreciated from the right panel in FIG. 14, the nucleic acid band in lane M1 disappeared, confirming that the nucleic acid was able to be collected from the electrophoresed gel.

DESCRIPTION OF THE REFERENCE NUMERALS

4 Gel plate
4a Segment
130 Adsorption mechanism (Contact control means)
131 First housing
132 Second housing
133 Actuator
135 Solenoid
136 Plunger
140 Magnet
142 Soft magnetic metal pin
150 Magnetic particles (trapping bodies)
350 Adsorption mechanism
352 Housing
354 Magnet device
356 Actuator
360 Magnet
362 Solenoid
365 Adsorption plate
370 Trapping bodies
402 Gel plate
405 First well plate
407 Second well plate
452 Gel plate
454 First well plate
456 Second well plate
465 Biologically-relevant substance
500 Adsorption mechanism
502 Soft magnetic metal pin
504 Coil
506 Microminiature pump
510 Aperture
512 Trapping bodies

The invention claimed is:

1. A device for trapping a biologically-relevant substance, which device comprises:
   (a) magnetic particles for trapping the biologically-relevant substance,
   (b) rod-like magnetic member being capable of retaining the magnetic particles on a tip of the magnetic member and releasing the magnetic particles from the tip,
   (c) an electrode for charging the magnetic member, and
   (d) a permanent magnet for retaining the magnetic particles,
   wherein the magnetic particles retained by the magnetic member are charged and brought into contact with
   (i) a predetermined position on a gel in which the biologically-relevant substance has been fractionated or
   (ii) a thin tissue section containing the biologically-relevant substance
   such that the biologically-relevant substance from said gel or thin tissue section is trapped, and
   wherein the magnetic member includes a conductive intermediate member that separates the magnetic particles from the permanent magnet, and serves as a cover for partitioning the permanent magnet from the magnetic particles.

2. The device according to claim 1, wherein the magnetic particles are magnetic particles bound with a substance having affinity for the biologically-relevant substance.

3. The device according to claim 1, wherein the magnetic particles are charged via the magnetic member.

4. The device according to claim 1, wherein the magnetic member is provided with a mechanism for magnetizing or demagnetizing the magnetic particles.

5. The device according to claim 1, wherein the biologically-relevant substance is a nucleic acid or a protein.

6. The device according to claim 1, wherein the magnetic member comprises one or more pins.

7. A method for collecting a biologically-relevant substance, which method comprises a step of using the device according to claim 1 to collect the biologically-relevant substance from (i) a gel in which the biologically-relevant substance has been fractionated or (ii) a thin tissue section containing the biologically-relevant substance.

* * * * *